(12) United States Patent
Kiraly et al.

(10) Patent No.: US 9,603,576 B2
(45) Date of Patent: Mar. 28, 2017

(54) VISUALIZATION OF DUAL ENERGY COMPUTED TOMOGRAPHY AIRWAYS DATA

(71) Applicant: Siemens Aktiengesellschaft, Munich (DE)

(72) Inventors: Atilla Peter Kiraly, Plainsboro, NJ (US); Benjamin L. Odry, West New York, NJ (US); Carol L. Novak, Newtown, PA (US)

(73) Assignee: Siemens Healthcare GmbH, Erlangen (DE)

( * ) Notice: Subject to any disclaimer, the term of this patent is extended or adjusted under 35 U.S.C. 154(b) by 20 days.

(21) Appl. No.: 14/484,393

(22) Filed: Sep. 12, 2014

(65) Prior Publication Data

US 2015/0086099 A1    Mar. 26, 2015

Related U.S. Application Data

(60) Provisional application No. 61/882,132, filed on Sep. 25, 2013.

(51) Int. Cl.
| | | |
|---|---|---|
| *A61B 6/00* | (2006.01) | |
| *A61B 6/03* | (2006.01) | |
| *G06T 7/00* | (2017.01) | |

(52) U.S. Cl.
CPC .............. *A61B 6/466* (2013.01); *A61B 6/032* (2013.01); *A61B 6/4241* (2013.01); *A61B 6/469* (2013.01); *A61B 6/482* (2013.01); *A61B 6/50* (2013.01); *G06T 7/0081* (2013.01); *G06T 2207/10081* (2013.01); *G06T 2207/10152* (2013.01); *G06T 2207/30061* (2013.01)

(58) Field of Classification Search
CPC ....... A61B 6/466; A61B 6/482; A61B 6/4241; A61B 6/469; A61B 6/50; A61B 6/032; G06T 7/0081; G06T 2207/10081; G06T 2207/30061; G06T 2207/10152
USPC ......................................................... 382/131
See application file for complete search history.

(56) References Cited

U.S. PATENT DOCUMENTS

| | | | | |
|---|---|---|---|---|
| 2007/0103464 A1* | 5/2007 | Kaufman | .............. | G06T 7/0012 345/424 |
| 2010/0328313 A1* | 12/2010 | Zamyatin | ............... | G06K 9/342 345/440 |

OTHER PUBLICATIONS

Walsh, S. L. F., A. Nair, and D. M. Hansell. "Post-processing applications in thoracic computed tomography." Clinical radiology 68.5 (2013): 433-448. May 2013.*
A. P. Kiraly, et al., "Three-Dimensional Human Airway Segmentation Methods for Clinical Virtual Bronchoscopy1," Academic Radiology, vol. 9, No. 10, pp. 1153-1168, 2002.
A. P. Kiraly, et al., "Three-Dimensional Path Planning for Virtual Bronchoscopy," IEEE Transactions on Medical Imaging, vol. 23, No. 9, pp. 1365-1379, Sep. 2004.

(Continued)

*Primary Examiner* — Amandeep Saini

(57) ABSTRACT

A method for depicting an airway tree of a patient includes: (a) generating an iodine map of the airway tree from dual energy computed tomography (DECT) imaging data acquired from the patient; (b) defining a region of interest of the airway tree from the DECT imaging data; (c) rendering at least a portion of the airway tree based on information derived from the iodine map and the defined region of interest; and (d) displaying a graphical image of at least a portion of the airway tree on a user interface. Systems for depicting an airway tree of a patient are described.

20 Claims, 5 Drawing Sheets

(56) References Cited

OTHER PUBLICATIONS

A. P. Kiraly, et al., "Boundary-Specific Cost Functions for Quantitative Airway Analysis," Med. Image Comput. Comput. Assist. Interv., 10 (Pt. 1), pp. 784-791, 2007.

B. L. Odry, et al., "Active contour approach for accurate quantitative airway analysis," in SPIE Proceedings vol. 6916: Medical Imaging 2008: Physiology, Function, and Structure from Medical Images, pp. 1-12, Mar. 2008.

B. L. Odry, et al., "Comparison of analysis methods for airway quantification," in SPIE Proceedings vol. 8315: Medical Imaging 2012: Computer-Aided Diagnosis, pp. 1-12, Feb. 2012.

D. Aykac, et al., "Segmentation and Analysis of the Human Airway Tree from Three-Dimensional X-Ray CT Images," IEEE Transactions on Medical Imaging, vol. 22, No. 8, pp. 940-950, Aug. 2003.

* cited by examiner

VISUALIZATION OF DUAL ENERGY COMPUTED TOMOGRAPHY AIRWAYS DATA

RELATED APPLICATIONS

This claims the benefit of U.S. Provisional Application No. 61/882,132, filed Sep. 25, 2013. The entire contents of the provisional application are incorporated herein by reference, except that in the event of any inconsistent disclosure or definition from the present specification, the disclosure or definition herein shall be deemed to prevail.

TECHNICAL FIELD

The present teachings relate generally to the visualization of airway trees and, in some embodiments, to the diagnosis and/or evaluation of pulmonary disease using visualizations of a patient's airway tree.

BACKGROUND

A thickening in the walls of the airways may be a result of scar tissue (e.g., permanent damage) or a potentially treatable tissue irritation. The airways in the lungs of a patient may be examined for anatomical defects using standard computed tomography (CT). However, it may not be possible to distinguish scar tissue from tissue irritation using a standard CT image alone.

The technique of dual energy computed tomography (DECT) may be used to obtain functional information from images of a patient's airways. In DECT, an image of a patient who has been injected intravenously with a contrast agent (e.g., iodine) may be captured using two different energy sources (e.g., a high-energy source and a low-energy source). In the dual energy images thus obtained, the iodine concentration may be differentiated from other materials (e.g., water and tissue). Since the intravenous iodine is in the blood, a determination of iodine concentration may indicate whether a thickened area results from scar tissue or from increased blood flow indicative of inflammation.

The resultant iodine map generated from DECT provides a complete volume of the patient including information that may be extraneous to the diagnosis and/or evaluation of an airway disease (e.g., chest wall, blood vessels, parenchyma, etc.). This extraneous information may reduce the overall efficacy and convenience of using a DECT-derived iodine map in a clinical and/or research environment.

SUMMARY

The scope of the present invention is defined solely by the appended claims, and is not affected to any degree by the statements within this summary.

In accordance with the present teachings, a visualization of a patient's airway walls from a computed iodine map obtained by dual energy computed tomography (DECT) is provided. The visualization derived from the computed iodine map may be presented in a bronchogram-like format familiar to radiologists. The bronchogram-like format is referred to herein as a bronchodine (e.g., a composite word derived from "bronchogram" and "iodine"), and depicts iodine concentration in regions of diagnostic interest (e.g., airway walls, etc.) while excluding extraneous regions (e.g., connective tissue, etc.) that are deemed distracting and unnecessary to diagnosis and/or evaluation. Methods in accordance with the present teachings may visualize an entire DECT dataset in 3D with minimal post-processing, thereby retaining a substantial portion of the original data.

By way of introduction, a computer-implemented method of depicting an airway tree of a patient in accordance with the present teachings includes: (a) generating an iodine map of the airway tree from dual energy computed tomography (DECT) imaging data acquired from the patient; (b) defining a region of interest of the airway tree from the DECT imaging data; (c) rendering at least a portion of the airway tree based on information derived from the iodine map and the defined region of interest; and (d) displaying a graphical image of at least a portion of the airway tree on a user interface.

A system for depicting an airway tree of a patient in accordance with the present teachings includes: (a) a processor; (b) a non-transitory memory coupled to the processor; (c) first logic stored in the memory and executable by the processor to cause the processor to generate an iodine map of the airway tree from dual energy computed tomography (DECT) imaging data acquired from the patient; (d) second logic stored in the non-transitory memory and executable by the processor to cause the processor to define a region of interest of the airway tree from the DECT imaging data; (e) third logic stored in the non-transitory memory and executable by the processor to cause the processor to render at least a portion of the airway tree based on information derived from the iodine map and the defined region of interest; and (f) fourth logic stored in the non-transitory memory and executable by the processor to cause the processor to display a graphical image of at least a portion of the airway tree on a user interface. In some embodiments, the third logic stored in the non-transitory memory is executable by the processor to cause the processor to render at least a portion of the airway tree based on information derived from the iodine map and limited to the defined region of interest of the airway tree.

A non-transitory computer readable storage medium in accordance with the present teachings has stored therein data representing instructions executable by a programmed processor for depicting an airway tree of a patient. The storage medium includes instructions for: (a) generating an iodine map of the airway tree from dual energy computed tomography (DECT) imaging data acquired from the patient; (b) defining a region of interest of the airway tree from the DECT imaging data; (c) rendering at least a portion of the airway tree based on information derived from the iodine map and the defined region of interest; and (d) displaying a graphical image of at least a portion of the airway tree on a user interface.

DETAILED DESCRIPTION

Figure 1:
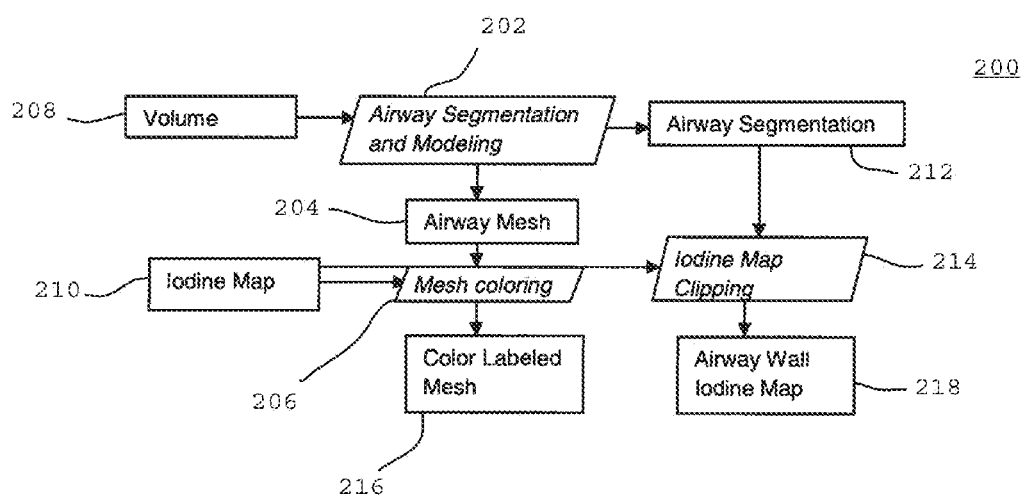
FIG. 1 shows a flow chart of a representative process 200 for depicting an airway tree of a patient in accordance with the present teachings.

To improve the phenotyping of airway diseases, blood perfusion may be measured via concentration of a contrast agent (e.g., iodine) using DECT imaging. The iodine maps thus obtained may be used to differentiate between scar tissue and inflamed airway walls. This level of differentiation may be helpful in indicating an optimum course of treatment for various pulmonary diseases, including but not limited to bronchiectasis, asthma, cystic fibrosis, and chronic obstructive pulmonary disease (COPD).

Iodine maps derived from DECT data may be useful in assessing airway morphology and blood perfusion in patients. In accordance with the present teachings, techniques for visualizing iodine maps that selectively focus on the airways of the patient have been developed and are described herein. In some embodiments, the methods may provide a bronchogram-like view of a patient's airway tree in a format that is familiar to radiologists. A conventional bronchogram is a radiograph of the bronchial tree made after a patient has been injected with a radiopaque substance.

By contrast to a conventional bronchogram, the view in a bronchodine in accordance with the present teachings may be limited to only that information that is considered relevant to the diagnosis and/or evaluation of airway disease. Extraneous information may be excluded from the bronchodine and post-processing of the original DECT data may be minimized. In some embodiments, as further described herein, the bronchodine may be obtained via surface rendering. In other embodiments, as further described herein, the bronchodine may be obtained via volume (e.g., projection) rendering.

As described above, techniques for depicting airway trees in accordance with the present teachings may involve minimal post-processing of data. Although sophisticated post-processing methods may be useful for simplifying or correcting views, computation errors may be introduced as a result, thereby compromising the interpretation of the data. Thus, the initial visualization of a patient's airway tree may be achieved from a bronchodine, thereby avoiding many post-processing errors. The bronchodine may be generated without bronchial tree quantification. For example, the bronchodine may be a mapping of the closest iodine value for each point on the 3D map as opposed to an average/maximum within a wall (e.g., a more complex calculation that would involve computing the wall dimensions at multiple locations within the branch). For methods in which the bronchodine is obtained via volume rendering, even less post processing may be involved since only a region near the segmentation may be used. In some embodiments, the bronchodine may be the sole visualization technique employed. In other embodiments, the bronchodine may be generated and one or more supplemental visualization techniques (e.g., that involve post-processing of data) may be used in addition.

It is to be understood that elements and features of the various representative embodiments described below may be combined in different ways to produce new embodiments that likewise fall within the scope of the present teachings.

By way of general introduction, an exemplary method for depicting an airway tree of a patient in accordance with the present teachings includes: (a) generating an iodine map of the airway tree from dual energy computed tomography (DECT) imaging data acquired from the patient; (b) defining a region of interest of the airway tree from the DECT imaging data; (c) rendering at least a portion of the airway tree based on information derived from the iodine map and the defined region of interest; and (d) displaying a graphical image of at least a portion of the airway tree on a user interface.

In some embodiments, a contrast agent other than, or in addition to, iodine may be used as an imaging agent in accordance with the present teachings. Representative alternative contrast agents include but are not limited to barium, air, carbon dioxide, and combinations thereof. If an imaging agent other than iodine is used, a map of the airway tree analogous to an iodine map may be generated from the DECT imaging data. Although in the description that follows iodine is described for use in the representative embodiments, it is to be understood that other types of contrast agents may be used.

In some embodiments, a method for depicting an airway tree of a patient in accordance with the present teachings is implemented using a computer and, in some embodiments, one or a plurality of the acts of (a) generating, (b) defining, (c) rendering, and/or (d) displaying described above are performed by one or a plurality of processors. The processors are able to render more quickly and consistently than a person. For time constrained medical environment, processor-based image generation assists diagnosis and/or treatment in ways that a human created image could not.

In some embodiments, the defined region of interest includes at least a portion of an airway wall and excludes information deemed to be extraneous to diagnosis and/or evaluation of a pulmonary disease. In some embodiments, the information deemed to be extraneous includes vasculature, parenchyma, or a combination thereof. In some embodiments, the graphical image displayed on the user interface indicates iodine concentration proximal to an airway wall.

In some embodiments, the defining of the region of interest includes segmenting and/or modeling an airway branch or branches (e.g., from one of the original volumes). In some embodiments, methods in accordance with the present teachings may operate on a given set of DECT volumes that contain the original low-energy volume and the computed iodine concentration volumes. In other embodiments, the high-energy volume or an "average" volume (computed, for example, from a weighted average of the low-energy volume and high-energy volume) may be used in place of the low-energy volume. Thus, in some embodiments, the DECT image acquired from the patient may be selected from a low-energy volume (e.g., 80 kV), a high-energy volume (e.g., 140 kV), an average volume (e.g., a weight average of the low-energy volume and the high-energy volume), and combinations thereof.

All manner of techniques for achieving the airway segmentation and model may be employed including but not limited to those described in an article entitled "Three-Dimensional Path Planning for Virtual Bronchoscopy" (*IEEE Transactions on Medical Imaging*, 2004, 23, No. 9, 1365-1379). The first step of the segmentation automatically identifies the trachea root site r within the dataset, and an adaptive threshold region growing method is used to obtain the airway lumen segmentation $l_s$ (as described, for example, in: "Three-Dimensional Human Airway Segmentation Methods for Clinical Virtual Bronchoscopy," *Academic Radiology,* 2002, 9, No. 10, 1153-1168). The segmented image $l_s$ and the root site r determine a tree model T through a process of skeletonization followed by stages of refinement (as described, for example, in: "Three-Dimensional Path Planning for Virtual Bronchoscopy," *IEEE Transactions on Medical Imaging,* 2004, 23, No. 9, 1365-1379). The model T=(S, B, P) is composed of a series of sites S, branches B, and paths P. Each site $s_i \in S$ identifies a 3D location within the image as well as a heading direction for the branch to which it belongs. Branches have parent and child branches that describe the hierarchy of the tree. The first branch, $b_0 \in B$, corresponds to the trachea, with the first site of that branch being r. The branch $b_0$ has no parent branches and two child branches: the left and right main bronchi. Terminal branches are the "leaves" of the tree with no further child branches. A path is a series of connected branches.

Obtaining the airway tree structure and hierarchy allows customization of the regions of interest in the final visualization. In some embodiments, the airway segmentation (e.g., the defining of the region of interest) may be computed from just the airway lumens (e.g., interior surface of the airway walls). Alternatively, the airway wall may be segmented based on the inner and outer boundaries of the airway walls in order to provide additional details and more precisely locate the wall. Since each site contains both a location and a directional heading, measurements perpendicular to the airway may be obtained. Representative methods for providing reliable measurements of the inner and outer walls of the airways include those described in (1) "Boundary-Specific Cost Functions for Quantitative Airway Analysis," *Med. Image Comput. Comput. Assist. Interv.* 2007, 10 (Pt. 1), 784-791; (2) "Active contour approach for accurate quantitative airway analysis," in *SPIE Proceedings Vol. 6916: Medical Imaging* 2008: *Physiology, Function, and Structure from Medical Images,* 691613 (12 Mar. 2008) (eds. Xiaoping P. Hu; Anne V. Clough); and (3) "Comparison of analysis methods for airway quantification," in *SPIE Proceedings Vol.* 8315: *Medical Imaging* 2012: *Computer-Aided Diagnosis,* 83152R (23 Feb. 2012) (eds. Bram van Ginneken; Carol L. Novak). For example, the full-width half maximum approach gauges the location of the airway wall based on half the intensity value of the maximum and minimum gray levels along a sampling direction in order to determine (a) the inner contour defining the division between the lumen and the inner surface of the airway wall and (b) the outer contour defining the division between the outer surface of the airway wall and the lung parenchyma.

In accordance with the present teachings, a bronchodine may be generated based on surface rendering or volume rendering. In some embodiments, only one of surface rendering and volume rendering is performed. In other embodiments, both surface rendering and volume rendering are performed. Differences between the two rendering approaches are described below in reference to FIG. 2.

For embodiments that involve volume rendering, the defined region of interest may include an airway segmentation, and the rendering may further include clipping the iodine map to excise one or more portions that lie outside the defined region of interest. In some embodiments, the rendering includes volume rendering on the iodine map masked by the airway segmentation. In some embodiments, the airway walls may not be segmented and a dilation of a segmented lumen may be used.

Figure 2A:
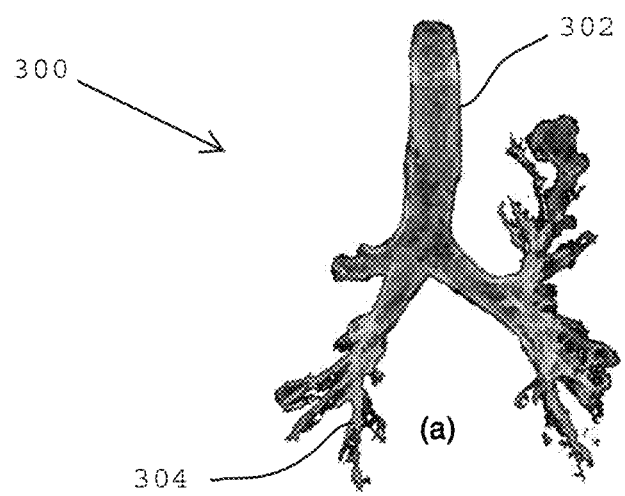
FIG. 2A shows an example of a dual-energy bronchodine depicting iodine concentration near an airway wall that was obtained via volume rendering.
Figure 2B:
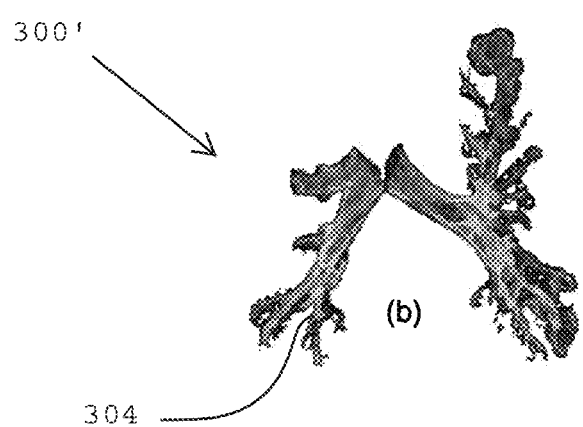
FIG. 2B shows an example of a volume-rendered bronchodine from which extraneous portions that were visible in FIG. 2A have been excised in order to focus on a region of interest containing the smaller, more peripheral airways.
Figure 2C:
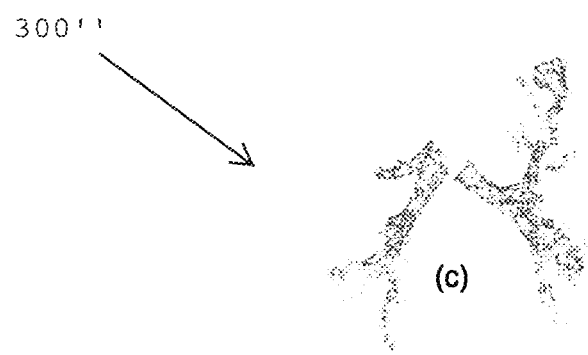
FIG. 2C shows an example of a volume-rendered bronchodine in which a threshold used in defining the region of interest is set to exclude extraneous vasculature that was visible in FIGS. 2A and 2B.

FIG. 2A shows an example of a volume-rendered dual-energy bronchodine depicting iodine concentration near the boundary of the lumen. Volume rendering of the iodine map masked by the airway lumen segmentation produces a bronchodine view of the airway tree 300. The visualization allows for a minimally filtered view of the data. In FIG. 2A, the complete airway tree 300 is rendered at a specific thickness. In FIG. 2B, the airway tree 300' differs from the airway tree 300 shown in FIG. 2A in that the trachea 302 (a region that may not be of interest to a radiologist) has not been rendered. In the airway tree 300' shown in FIG. 2B, the focus has instead been placed on the more peripheral, smaller airways. FIGS. 2B and 2C show the same dataset volume rendered with different thickness levels around the lumen segmentation. In FIG. 2C, the airway tree 300" depicts a thinner portion near the airway lumen in order to exclude the extraneous blood vessels 304 that are visible in FIGS. 2A and 2B. The transfer function for the volume rendering may be defined to take into account transparency between differing iodine levels. For example, higher iodine concentrations may be made more opaque so that they are more visible, thereby facilitating visualization of nearby vessels 304 as shown in FIGS. 2A and 2B. Thus, in some embodiments, the rendering of at least a portion of the airway tree based on information derived from the iodine map and the defined region of interest includes defining a transfer function whereby a higher concentration of iodine is correlated with an increased opacity.

For embodiments that involve surface rendering, the defined region of interest may include a mesh of the airway tree surface and the rendering may further include coloring the mesh based on colors obtained from the iodine map (e.g., using a transfer function). A surface mesh is a representation of only the outer surface of the segmentation, and is typically composed of a set of small connected polygons. In some embodiments, each point of the mesh is colored with a single value from the closest position in the iodine map. In other embodiments, the single color value may be computed from an average of values from the iodine map.

Figure 2D:
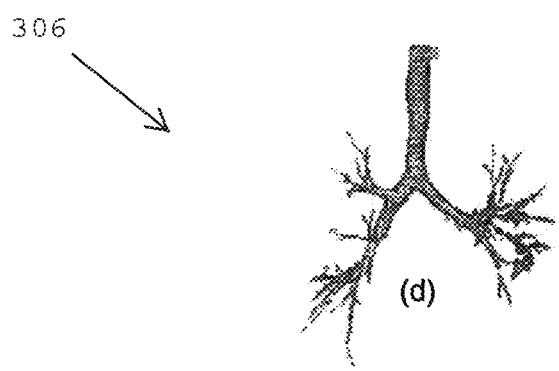
FIG. 2D shows an example of a colored mesh of a representative airway tree that was obtained via surface rendering.

By way of example, FIG. 2D shows an example of a surface-rendered mesh 306 of the airway tree that has been colored based on the iodine map. Unlike the volume renderings shown in FIGS. 2A, 2B, and 2C, which display iodine values within variable thickness off of the lumen, the surface-rendered colored mesh 306 shown in FIG. 2D does not expand beyond the lumen (no variable thickness) and only contains a single point from the iodine map as a color. This single value point may be the actual iodine value at the corresponding location, or a computed value based on the iodine at the corresponding point/airway wall (e.g., iodine average within the airway wall). Whereas with volume rendering, a series of voxels of any thickness may be rendered, surface rendering may be limited to a single color at the surface, such that a decision is made as to what this color should be. In some embodiments, the color may be an average of voxel values or a function of voxel values to help encode that information into a single point.

FIG. 1 shows a flow chart of a representative process 200 for producing a bronchodine to depict an airway tree of a patient in accordance with the present teachings. In FIG. 1, the parallelograms represent exemplary acts in the process 200, whereas the rectangles represent outputs/inputs/data generated by these acts. For example, the act 202 of "airway segmentation and modeling" may result in an output of an "airway mesh" 204 and/or an "airway segmentation" 212. The act 206 of "mesh coloring" may result in an output of a "color labeled mesh" 216. The act 214 of "iodine map clipping" may result in an output of an "airway wall iodine map" 218. As shown in FIG. 1, the "color labeled mesh" 216 is the output for surface rendering, and the "airway wall iodine map" 218 is the output for volume rendering.

The process shown in FIG. 1 includes two inputs: the "volume" 208 (e.g., the original 80 kV volume, the original 140 kV volume, or an averaged volume) and the computed "iodine map" 210. Regardless of whether rendering is based on surface rendering or volume rendering, the act 202 of "airway segmentation and modeling" may be performed using, for example, a method as described in the above-cited literature reference. Any segmentation may be used to identify locations in the volume associated with airway passages. The resultant "airway segmentation" 212 may be used to mask the "iodine map" 210 and volume render the results directly. The mask indicates locations (e.g., tissue of airway branches) for which iodine information is of interest, masking out other locations (e.g., voxels not at or within a thickness range of the airway branches). Alternatively, the "airway mesh" 204 obtained via "airway segmentation and modeling" 202 may be used instead. The vertices of the "airway mesh" 204 are colored based on the "iodine map" 210. Both rendering approaches involve defining a transfer function to show the iodine concentration at the airway passages.

It is to be understood that the relative ordering of some acts shown in the flow chart of FIG. 1 is meant to be merely representative rather than limiting, and that alternative sequences may be followed. Moreover, it is likewise to be understood that additional, different, or fewer acts may be provided and that one or more of these acts may occur in a different sequential order and/or substantially contemporaneously.

In some embodiments, as described above, the present teachings provide methods for depicting an airway tree of a patient. In other embodiments, as further described below, the present teachings also provide systems for depicting an airway tree of a patient.

In some embodiments, a system 400 for depicting an airway tree of a patient in accordance with the present teachings is implemented as part of an imaging module in a computer system. A representative x-ray CT system that may be used in accordance with the system 400 may include one or more x-ray sources (e.g., two x-ray sources for dual energy CT) and corresponding detectors, wherein the sources and the detectors are located on opposite arms of a rotating gantry.

Figure 3:
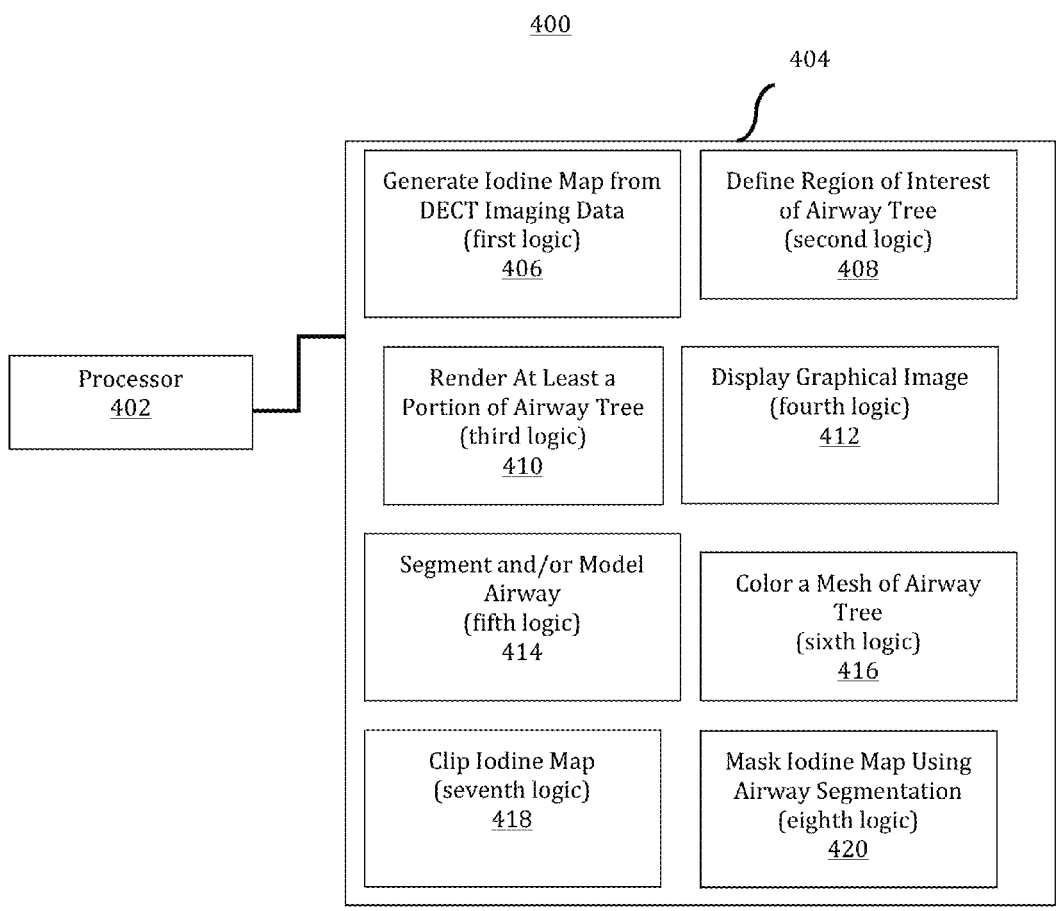
FIG. 3 shows a block diagram of a representative system for depicting an airway tree of a patient in accordance with the present teachings.

FIG. 3 shows a block diagram of a representative system 400 in accordance with the present teachings. In some embodiments, as shown in FIG. 3, the system 400 includes: a processor 402; a non-transitory memory 404 coupled with the processor 402; first logic 406 stored in the non-transitory memory 404 and executable by the processor 402 to cause the processor 402 to generate an iodine map of the airway tree from dual energy computed tomography (DECT) imaging data acquired from the patient; second logic 408 stored in the non-transitory memory 404 and executable by the processor 402 to cause the processor 402 to define a region of interest of the airway tree from the DECT imaging data; third logic 410 stored in the non-transitory memory 404 and executable by the processor 402 to cause the processor 402 to render at least a portion of the airway tree based on information derived from the iodine map and the defined region of interest; and fourth logic 412 stored in the non-transitory memory 404 and executable by the processor 402 to cause the processor 402 to display a graphical image of at least a portion of the airway tree on a user interface.

In some embodiments, the apparatus 400 may further include one or more of the following: fifth logic 414 stored in the non-transitory memory 404 and executable by the processor 402 to cause the apparatus 400 to segment and/or model an airway branch or branches; sixth logic 416 stored in the non-transitory memory 404 and executable by the processor 402 to cause the apparatus 400 to color a mesh of the airway tree based on the iodine map; seventh logic 418 stored in the non-transitory memory 404 and executable by the processor 402 to cause the apparatus 400 to clip the iodine map to excise one or more portions that lie outside the defined region of interest; and/or eighth logic 420 stored in the non-transitory memory 404 and executable by the processor 402 to cause the apparatus 400 to mask the iodine map using an airway segmentation.

In some embodiments, the system 400 may be coupled to other modules of a computer system and/or to databases so as to have access to relevant information as needed (e.g., DECT imaging data, patient identification information, physician and/or technician identification information, etc.) and initiate appropriate actions.

A non-transitory computer-readable storage medium in accordance with the present teachings has stored therein data representing instructions executable by a programmed processor for depicting an airway tree of a patient. The storage medium includes instructions for: (a) generating an iodine map of the airway tree from dual energy computed tomography (DECT) imaging data acquired from the patient; (b) defining a region of interest of the airway tree from the DECT imaging data; (c) rendering at least a portion of the airway tree based on information derived from the iodine map and the defined region of interest; and (d) displaying a graphical image of at least a portion of the airway tree on a user interface.

One or more modules or logic described herein may be implemented using, among other things, a tangible computer-readable medium comprising computer-executable instructions (e.g., executable software code). Alternatively, modules may be implemented as software code, firmware code, hardware, and/or a combination of the aforementioned. For example the modules may be embodied as part of a medical imaging system.

Figure 4:
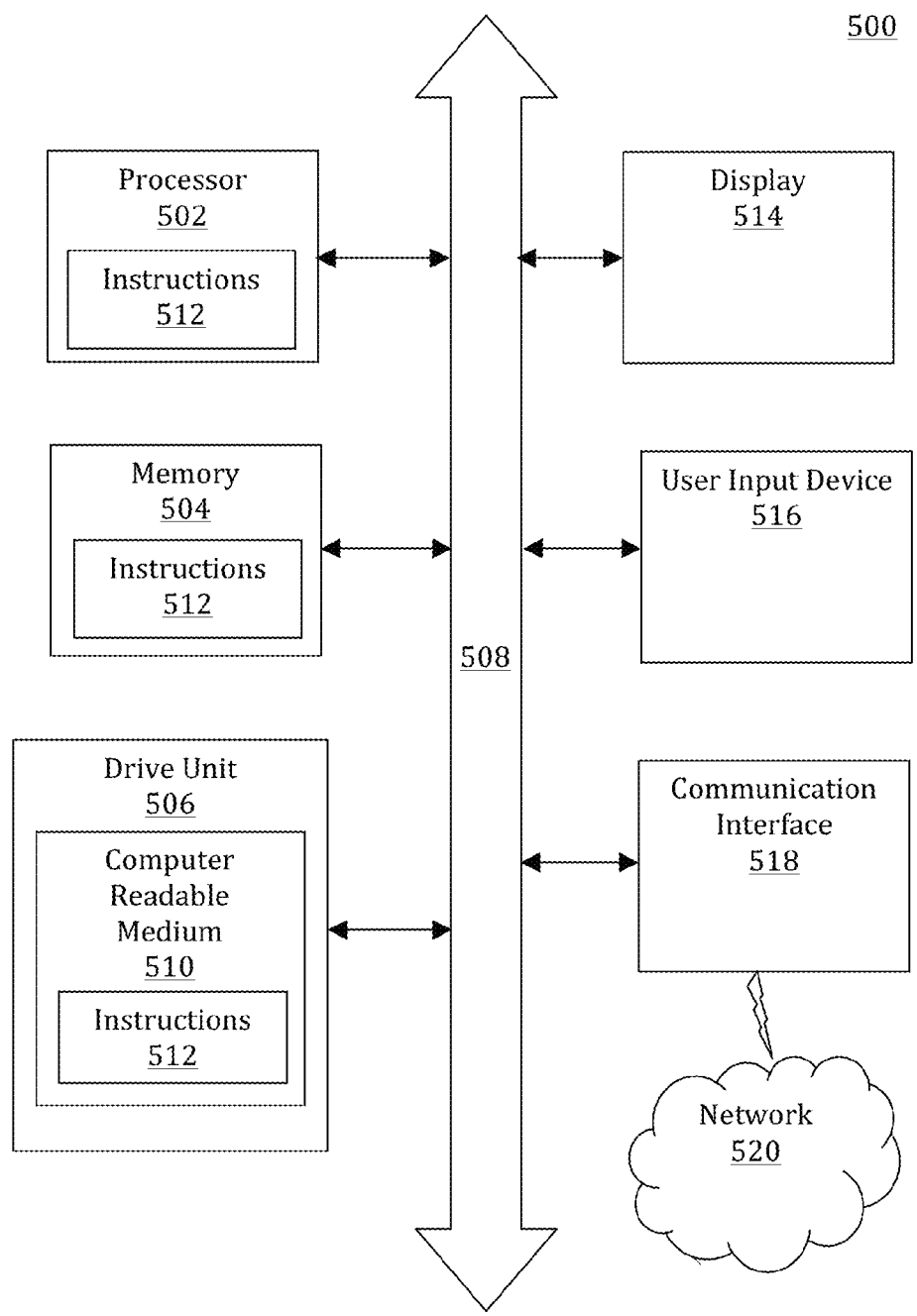
FIG. 4 shows a representative general computer system for use with a system in accordance with the present teachings.

FIG. 4 depicts an illustrative embodiment of a general computer system 500. The computer system 500 can include a set of instructions that can be executed to cause the computer system 500 to perform any one or more of the methods or computer based functions disclosed herein. The computer system 500 may operate as a standalone device or may be connected (e.g., using a network) to other computer systems or peripheral devices. Any of the components discussed above, such as the processor, may be a computer system 500 or a component in the computer system 500. The computer system 500 may implement an imaging module, of which the disclosed embodiments are a component thereof.

In a networked deployment, the computer system 500 may operate in the capacity of a server or as a client user computer in a client-server user network environment, or as a peer computer system in a peer-to-peer (or distributed) network environment. The computer system 500 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In some embodiments, the computer system 500 may be implemented using electronic devices that provide voice, video or data communication. Further, while a single computer system 500 is illustrated, the term "system" shall also be taken to include any collection of systems or sub-systems that individually or jointly execute a set, or multiple sets, of instructions to perform one or more computer functions.

As shown in FIG. 4, the computer system 500 may include a processor 502, for example a central processing unit (CPU), a graphics-processing unit (GPU), or both. The processor 502 may be a component in a variety of systems. For example, the processor 502 may be part of a standard personal computer or a workstation. The processor 502 may be one or more general processors, digital signal processors, application specific integrated circuits, field programmable gate arrays, servers, networks, digital circuits, analog circuits, combinations thereof, or other now known or later developed devices for analyzing and processing data. The processor 502 may implement a software program, such as code generated manually (i.e., programmed).

The computer system 500 may include a memory 504 that may communicate via a bus 508. The memory 504 may be a main memory, a static memory, or a dynamic memory. The memory 504 may include, but is not limited to, computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In some embodiments, the memory 504 includes a cache or random access memory for the processor 502. In alternative embodiments, the memory 504 is separate from the processor 502, such as a cache memory of a processor, the system memory, or other memory. The memory 504 may be an external storage device or database for storing data. Examples include a hard drive, compact disc (CD), digital video disc (DVD), memory card, memory stick, floppy disc, universal serial bus (USB) memory device, or any other device operative to store data. The memory 504 is operable to store instructions executable by the processor 502. The functions, acts or tasks illustrated in the figures or described herein may be performed by the programmed processor 502 executing the instructions 512 stored in the memory 504. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown in FIG. 4, the computer system 500 may further include a display unit 514, such as a liquid crystal display (LCD), an organic light emitting diode (OLED), a flat panel display, a solid state display, a cathode ray tube (CRT), a projector, a printer or other now known or later developed display device for outputting determined information. The display 514 may act as an interface for the user to see the functioning of the processor 502, or specifically as an interface with the software stored in the memory 504 or in the drive unit 506. A value or image depicting at least a portion of a patient's airway tree may be output to a user (e.g., a physician, technician, etc.) on the display unit 514. For example, an image (e.g., a bronchodine) representing at least a portion of the patient's airway tree together with identifying information (e.g., alphanumeric text) may be provided in the graphical image.

Additionally, as shown in FIG. 4, the computer system 500 may include an input device 516 configured to allow a user to interact with any of the components of system 500. The input device 516 may be a number pad, a keyboard, or a cursor control device, such as a mouse, or a joystick, touch screen display, remote control or any other device operative to interact with the system 500.

In some embodiments, as shown in FIG. 4, the computer system 500 may also include a disk or optical drive unit 506. The disk drive unit 506 may include a computer-readable medium 510 in which one or more sets of instructions 512 (e.g., software) may be embedded. Further, the instructions 512 may embody one or more of the methods or logic as described herein. In some embodiments, the instructions 512 may reside completely, or at least partially, within the memory 504 and/or within the processor 502 during execution by the computer system 500. The memory 504 and the processor 502 also may include computer-readable media as described above.

The present teachings contemplate a computer-readable medium that includes instructions 512 or receives and executes instructions 512 responsive to a propagated signal, so that a device connected to a network 520 may communicate voice, video, audio, images or any other data over the network 520. Further, the instructions 512 may be transmitted or received over the network 520 via a communication interface 518. The communication interface 518 may be a part of the processor 502 or may be a separate component. The communication interface 518 may be created in software or may be a physical connection in hardware. The communication interface 518 is configured to connect with a network 520, external media, the display 514, or any other components in system 500, or combinations thereof. The connection with the network 520 may be a physical connection, such as a wired Ethernet connection or may be established wirelessly as discussed below. Likewise, the additional connections with other components of the system 500 may be physical connections or may be established wirelessly.

The network 520 may include wired networks, wireless networks, or combinations thereof. The wireless network may be a cellular telephone network, an 802.11, 802.16, 802.20, or WiMax network. Further, the network 520 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification may be implemented in digital electronic circuitry, or in computer software, firmware, or hardware, including the structures disclosed in this specification and their structural equivalents, or in combinations of one or more of them. Embodiments of subject matter described in this specification may be implemented as one or more computer program products, for example, one or more modules of computer program instructions encoded on a computer-readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer-readable medium may be a machine-readable storage device, a machine-readable storage substrate, a memory device, or a combination of one or more of them. The term "data processing apparatus" encompasses all apparatuses, devices, and machines for processing data, including but not limited to, by way of example, a programmable processor, a computer, or multiple processors or computers. The apparatus may include, in addition to hardware, code that creates an execution environment for the computer program in question (e.g., code that constitutes processor firmware, a protocol stack, a database management system, an operating system, or a combination thereof).

In some embodiments, the computer-readable medium may include a solid-state memory such as a memory card or other package that houses one or more non-volatile read-only memories. Further, the computer-readable medium may be a random access memory or other volatile rewritable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the present teachings are considered to include any one or more of a computer-readable medium or a distribution medium and other equivalents and successor media, in which data or instructions may be stored.

In some embodiments, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In some embodiments, the methods described herein may be implemented by software programs executable by a computer system. Further, in some embodiments, implementations may include distributed processing, component/object distributed processing, and parallel processing. Alternatively, virtual computer system processing may be constructed to implement one or more of the methods or functionality as described herein.

Although the present teachings describe components and functions that may be implemented in particular embodiments with reference to particular standards and protocols, the present invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described herein may be performed by one or more programmable processors executing one or more computer programs to perform functions by operating on input data and generating output. The processes and logic flows may also be performed by, and apparatus may also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The main elements of a computer are a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer may be embedded in another device, for example, a mobile telephone, a personal digital assistant (PDA), a mobile audio player, a Global Positioning System (GPS) receiver, to name just a few. Computer-readable media suitable for storing computer program instructions and data include all forms of non volatile memory, media and memory devices, including but not limited to, by way of example, semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, some embodiments of subject matter described herein may be implemented on a device having a display, for example a CRT (cathode ray tube) or LCD (liquid crystal display) monitor, for displaying information to the user and a keyboard and a pointing device, for example a mouse or a trackball, by which the user may provide input to the computer. Other kinds of devices may be used to provide for interaction with a user as well. By way of example, feedback provided to the user may be any form of sensory feedback (e.g., visual feedback, auditory feedback, or tactile feedback); and input from the user may be received in any form, including but not limited to acoustic, speech, or tactile input.

Embodiments of subject matter described herein may be implemented in a computing system that includes a back-end component, for example, as a data server, or that includes a middleware component, for example, an application server, or that includes a front end component, for example, a client computer having a graphical user interface or a Web browser through which a user may interact with an implementation of the subject matter described in this specification, or any combination of one or more such back end, middleware, or front end components. The components of the system may be interconnected by any form or medium of digital data communication, for example, a communication network. Examples of communication networks include but are not limited to a local area network (LAN) and a wide area network (WAN), for example, the Internet.

The computing system may include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 CFR §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

What is claimed is:

1. A computer-implemented method of depicting an airway tree of a patient, the method comprising:
   generating, by a computed tomography system, an iodine map of the airway tree from dual energy computed tomography (DECT) imaging data acquired from the patient;
   performing, by the computed tomography system, segmentation and modeling defining a region of interest of the airway tree for rendering from the DECT imaging data, the defined region of interest including at least a portion of the airway tree and excluding at least a different portion of the airway tree; then
   rendering the region of interest of the airway tree with information derived from the generated iodine map based on the airway segmentation and modeling from the DECT imaging data; and
   displaying a graphical image of the region of interest of the airway tree on a user interface.

2. The computer-implemented method of claim 1 wherein the performing the airway segmentation and modeling defining the region of interest comprises segmenting and/or modeling an airway branch or branches.

3. The computer-implemented method of claim 1 wherein the rendering comprises surface rendering.

4. The computer-implemented method of claim 3 wherein the defined region of interest comprises a mesh of the airway tree, and wherein the rendering further comprises coloring the mesh based on the iodine map.

5. The computer-implemented method of claim 4 wherein the coloring of the mesh uses a transfer function.

6. The computer-implemented method of claim 1 wherein the rendering comprises volume rendering.

7. The computer-implemented method of claim 6 wherein the defined region of interest comprises an airway segmentation, and wherein the rendering further comprises clipping the iodine map to excise one or more portions that lie outside the defined region of interest.

8. The computer-implemented method of claim 6 wherein the rendering comprises masking the iodine map using an airway segmentation.

9. The computer-implemented method of claim 6 wherein the rendering comprises defining a transfer function whereby a higher concentration of iodine is assigned with an increased opacity than a lower concentration.

10. The computer-implemented method of claim 1 wherein the defined region of interest excludes information of the airway tree above a threshold size.

11. The computer-implemented method of claim 10 wherein the excluded portion of the airway tree comprises vasculature, parenchyma, or a combination thereof.

12. The computer-implemented method of claim 1 wherein the DECT imaging data comprises a low-energy volume, a high-energy volume, a weighted average of the low-energy volume and the high-energy volume, or a combination thereof.

13. The computer-implemented method of claim 1 wherein the performing segmentation and modeling defining of the region of interest comprises segmenting an airway branch based on an interior surface of an airway wall.

14. The computer-implemented method of claim 1 wherein the performing segmentation and modeling defining of the region of interest comprises segmenting an airway branch based on an interior surface and an exterior surface of an airway wall.

15. The computer-implemented method of claim 1 wherein the graphical image displayed on the user interface indicates iodine concentration proximal to an airway wall.

16. A system for depicting an airway tree of a patient, the system comprising:
 a processor;
 a non-transitory memory coupled with the processor;
 first logic stored in the non-transitory memory and executable by the processor to cause the processor to generate an iodine map of the airway tree from dual energy computed tomography (DECT) imaging data acquired from the patient;
 second logic stored in the non-transitory memory and executable by the processor to cause the processor to segment and/or model a region of interest of the airway tree for rendering from the DECT imaging data, the region of interest including at least a portion of the airway tree and excluding at least a different portion of the airway tree;
 third logic stored in the non-transitory memory and executable by the processor to cause the processor to render the region of interest of the airway tree with information derived from the generated iodine map based on the airway segmentation and modeling from the DECT imaging data; and
 fourth logic stored in the non-transitory memory and executable by the processor to cause the processor to display a graphical image of the region of interest of the airway tree on a user interface.

17. The system of claim 16 wherein the second logic is stored in the non-transitory memory and executable by the processor to cause the processor to segment and/or model an airway branch or branches.

18. The system of claim 16 further comprising:
 fifth logic stored in the non-transitory memory and executable by the processor to cause the processor to color a mesh of the airway tree based on the iodine map.

19. The system of claim 16 further comprising:
 fifth logic stored in the non-transitory memory and executable by the processor to cause the processor to clip the iodine map to excise one or more portions that lie outside the defined region of interest; and
 sixth logic stored in the non-transitory memory and executable by the processor to cause the processor to mask the iodine map using an airway segmentation.

20. A non-transitory computer-readable storage medium having stored therein data representing instructions executable by a programmed processor for depicting an airway tree of a patient, the storage medium comprising instructions for:
 generating an iodine map of the airway tree from dual energy computed tomography (DECT) imaging data acquired from the patient;
 segmenting and modeling a defined region of interest of the airway tree for rendering from the DECT imaging data, the defined region of interest including at least a portion of the airway tree and excluding at least a different portion of the airway information tree;
 rendering the region of interest of the airway tree with information derived from the generated iodine map based on the airway segmentation and modeling from the DECT imaging data; and
 displaying a graphical image of at least a portion of the airway tree on a user interface.

* * * * *